United States Patent
Ergler et al.

(10) Patent No.: US 10,120,082 B2
(45) Date of Patent: Nov. 6, 2018

(54) ASCERTAINING AN ELECTRICAL DIRECT CURRENT COMPONENT IN THE CONVERTER ELEMENT

(71) Applicant: Siemens Healthcare GmbH, Erlangen (DE)

(72) Inventors: Thorsten Ergler, Erlangen (DE); Edgar Goederer, Forchheim (DE); Michael Hosemann, Erlangen (DE); Kurt Stadlthanner, Fuerth (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/440,298

(22) Filed: Feb. 23, 2017

(65) Prior Publication Data

US 2017/0254907 A1    Sep. 7, 2017

(30) Foreign Application Priority Data

Mar. 7, 2016  (DE) .................. 10 2016 203 665

(51) Int. Cl.
*G01T 1/18*     (2006.01)
*A61B 6/03*     (2006.01)
*A61B 6/00*     (2006.01)

(52) U.S. Cl.
CPC .............. *G01T 1/18* (2013.01); *A61B 6/4241* (2013.01)

(58) Field of Classification Search
CPC .. G01T 1/18; A61B 6/03; A61B 6/037; A61B 6/032
See application file for complete search history.

(56) References Cited

U.S. PATENT DOCUMENTS

2002/0109091 A1*  8/2002  Overdick ............ G01N 23/046
                                              250/336.1
2015/0069252 A1    3/2015  Eichenseer
(Continued)

FOREIGN PATENT DOCUMENTS

DE    102012213484 A1    2/2014
DE    102013217941 A1    3/2015

OTHER PUBLICATIONS

Krüger, H. et. al.: "CIX—A Detector for Spectral Enhanced X-ray Imaging by Simultaneous Counting and Integrating", in: SPIE Medical Imaging Conference, San Diego, 2008, DOI 10.1117/12.771706.
(Continued)

*Primary Examiner* — David Porta
*Assistant Examiner* — Faye Boosalis
(74) *Attorney, Agent, or Firm* — Harness, Dickey & Pierce, P.L.C.

(57) ABSTRACT

A counting X-ray detector for converting X-ray radiation into electrical signal pulses is disclosed. The counting X-ray detector includes, in a stacked arrangement, an illumination layer, a converter element and an evaluation unit. The illumination layer is designed to illuminate the converter element. The evaluation unit includes a measuring device for ascertaining an electrical direct current component in the converter element and a counting device for ascertaining from the signal pulses a number or an energy of events. A measuring electrode is formed on the converter element and an electrically conducting connection is formed between the measuring electrode and the measuring device.

31 Claims, 9 Drawing Sheets

(56) References Cited

U.S. PATENT DOCUMENTS

2015/0212215 A1\* 7/2015 Goderer .................... G01T 1/24
378/19
2015/0260856 A1\* 9/2015 Dierre ................ H01L 31/0224
250/370.09

OTHER PUBLICATIONS

Homogene Sensorausleuchtung mit Lichtleiter: published Nov. 24, 2014.
German Office Action dated Nov. 8, 2016.

\* cited by examiner

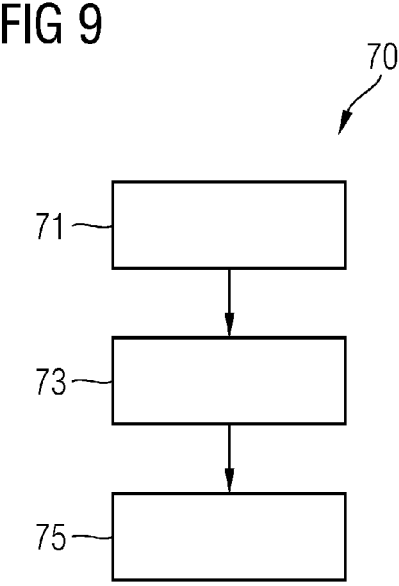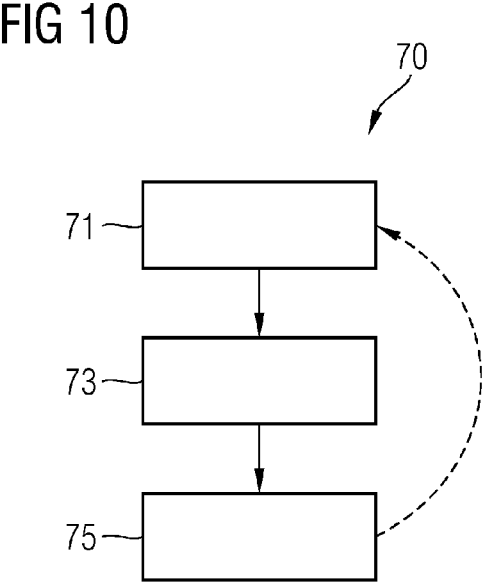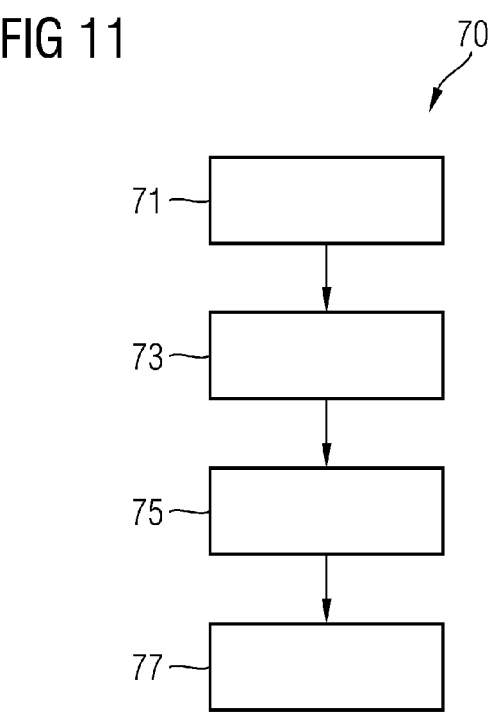

ASCERTAINING AN ELECTRICAL DIRECT CURRENT COMPONENT IN THE CONVERTER ELEMENT

PRIORITY STATEMENT

The present application hereby claims priority under 35 U.S.C. § 119 to German patent application number DE 102016203665.3 filed Mar. 7, 2016, the entire contents of which are hereby incorporated herein by reference.

FIELD

At least one embodiment of the invention generally relates to an X-ray detector, to a detector module, to a system, to a medical apparatus and/or to a method, wherein it is made possible to ascertain an electrical direct current component in the converter material and to stabilize the state of a converter element, of an X-ray detector or of a detector module.

BACKGROUND

Direct-conversion counting X-ray detectors are used in X-ray imaging, for example in computed tomography, angiography or radiography. The X-ray radiation or the photons can be converted into electrical signal pulses by a suitable sensor. Counting X-ray detectors not only allow counting of events but also facilitate information about the energy of the detected X-ray quant. This creates new opportunities in medical imaging for analysis and evaluation of the signal pulses.

Materials that can be used for the sensor as the converter material for the converter element are, for example, CdTe, CZT, CdZnTeSe, CdTeSe, CdMnTe, InP, $TlBr_2$, $HgI_2$, GaAs or other materials. The energy of the incident ionizing radiation is converted directly into electrical charges known as electron-hole pairs. A high voltage, for instance a voltage in the range of −500 to −2000V for CdTe, CZT, CdZnTeSe, CdTeSe or CdMnTe, is applied to the converter element between one electrode as the cathode and another electrode as the anode in order to separate the charges of the electron-hole pairs produced in the converter element. The cathode can be in the form of a continuous electrode. The anode can be in the form of a pixelated electrode. The high voltage is applied to the electrode by way of an external high-voltage source via an electrically conducting contact. X-ray quanta can produce electron-hole pairs in the converter element by energy deposition. The electron-hole pairs are separated by the applied high voltage, and the charge carriers, which are selected by the polarity of the high voltage, can be extracted or allowed to drift to the anode. It is thereby possible to produce an electrical signal pulse in the readout unit and/or the evaluation unit. The converter element is typically joined face-to-face in a stacked arrangement to a readout unit and/or an evaluation unit, for example to an integrated circuit (Application Specific Integrated Circuit, ASIC), via solder joints, electrically conductive adhesives or other techniques. The electrical signal pulses are evaluated by an evaluation unit, for instance an ASIC. The stacked arrangement comprising the converter element and the readout and/or evaluation unit is joined to a further substrate, for instance a printed circuit board, a ceramic substrate such as HTCC or LTCC, for example, or others. The electrical connections for the readout of the readout unit and/or the evaluation unit can be formed by way of through-silicon vias (TSV) or wire bonding.

In counting X-ray detectors, the detection characteristics can be stabilized over time and made spatially uniform by exposing the detector material continuously to an additional illumination. As happens with exposure to X-ray radiation, the additional illumination creates electron-hole pairs in the detector material which can be extracted by way of the high voltage. The higher the luminous energy incident on the detector from the additional illumination, the more electron-hole pairs are generated and the higher is a resultant direct current component, known as the sensor bias current (SBC). The luminous energy of the additional illumination and the uniformity of the illumination of the converter element can modify the drift behavior of the detector device.

In image acquisition, unacceptable image artifacts can arise due to undesirable polarization effects. The publication "Homogene Sensorausleuchtung mit Lichtleiter" ("Homogenous sensor illumination using light guide") by P. Sievers et al., 2014, Prior Art Journal, DOI 10.4421/PAPDEOTT003771 discloses that polarization effects can be curbed by an additional illumination, for example in the visible or infrared region. By using a detector having a diffuser for coupling-in light at the sensor surface it is possible to achieve a more uniform light-intensity distribution compared with LED circuit boards, which can be installed between anti-scatter grid and sensor.

Document US 2002/0109091 A1 discloses an X-ray detector comprising at least one converter unit for converting absorbed X-ray quanta into electrical charge signals, at least one evaluation unit for amplifying and further processing of the charge signals, and at least one data processing unit for the acquisition, further processing and output of the data. The charge signals are first amplified by an input amplifier in the evaluation unit, after which they are evaluated in parallel in a counting channel and in an integrating channel.

The publication "CIX—A Detector for Spectral Enhanced X-ray Imaging by Simultaneous Counting and Integrating" by H. Krüger et al., 2008, SPIE Medical Imaging Conference, San Diego, DOI 10.1117/12.771706 discloses a hybrid pixel detector, the design of which is based on simultaneous charge integration and photon counting.

Detector devices in computed tomography machines are constructed from a multiplicity of X-ray detectors or detector modules. For instance, some 20 to 50 detector modules can be arranged in a detector device. The detector modules are mounted in the radial direction, separated by the narrowest possible gap along the rotational axis. Each of these detector modules is illuminated separately in this arrangement by the additional illumination. As a result, the additional illumination from adjacent detector modules may be incident on adjacent converter elements. This can affect the signal stability of the detector modules. In order to avoid image artifacts, it is desirable that all the detector modules behave in the same manner. The inventors have found that it is desirable for the direct current component produced by the additional illumination to be the same in all the modules. It is desirable to adjust the illumination of the detector modules in such a way that the direct current component induced in the converter element is the same for each detector module. In practice, however, this is not the case because of manufacturing tolerances, for instance of the diffuser, potentially resulting in different module characteristics. The aim is to achieve uniform additional illumination over the entire detector device and to adjust the additional illumination accordingly.

SUMMARY

In least one embodiment of the invention, an X-ray detector, a detector module, a system, a medical apparatus and/or a method makes it possible to ascertain an electrical direct current component in the converter material and/or to stabilize the state of a converter element, of an X-ray detector or of a detector module.

At least one embodiment of the invention is directed to an X-ray detector. At least one embodiment of the invention is directed to a detector module. At least one embodiment of the invention is directed to a system. At least one embodiment of the invention is directed to a medical apparatus. At least one embodiment of the invention is directed to a method.

In various embodiments, the inventors propose a method and/or devices that can be used to ascertain the direct current component at low cost and even in individual sub-units of an X-ray detector.

At least one embodiment of the invention relates to a counting X-ray detector for converting X-ray radiation into electrical signal pulses. The X-ray detector comprises in a stacked arrangement an illumination layer, a converter element and an evaluation unit. The illumination layer is designed to illuminate the converter element. The X-ray detector comprises a measuring device for ascertaining an electrical direct current component in the converter element when illumination is active. The evaluation unit comprises a counting device for ascertaining from the signal pulses a number or an energy of events.

At least one embodiment of the invention also generally relates to a detector module comprising at least one X-ray detector according to at least one embodiment of the invention. A plurality of measuring devices can advantageously be formed in the detector module in order to obtain information about the direct current component that is as spatially precise as possible.

At least one embodiment of the invention also relates to a system comprising an X-ray detector or a detector module and to a control system, wherein the direct current component is an input signal to the control system. The control system can be an open-loop control system. The control system can control the additional illumination and/or the temperature. The control can advantageously be performed in spatial proximity to the X-ray detector and without long-distance data transfer.

At least one embodiment of the invention also relates to a medical apparatus comprising an X-ray detector according to at least one embodiment of the invention or a detector module according to at least one embodiment of the invention or a system according to at least one embodiment of the invention. A homogeneous or uniform state of the X-ray detectors inside the detector device can advantageously be achieved. Artifacts in the imaging can advantageously be prevented or reduced.

At least one embodiment of the invention also relates to a method for stabilizing a state of a converter element, of an X-ray detector or of a detector module, comprising the steps of illumination, ascertainment and adjustment. In the illumination step, the converter element is illuminated by a first luminous energy, which is emitted by the illumination layer. In the ascertainment step, a direct current component in the converter element is ascertained when illumination is active. In the step of adjusting a second luminous energy of an illumination and/or a temperature of a heating element as a function of the ascertained direct current component, the temperature or the illumination can be adjusted.

BRIEF DESCRIPTION OF THE DRAWINGS

Example embodiments of the invention are described in greater detail below with reference to drawings, in which:

FIG. 9 is a schematic diagram of a method according to the invention in a first embodiment;

FIG. 10 is a schematic diagram of a method according to the invention in a second embodiment; and FIG. 11 is a schematic diagram of a method according to the invention in a third embodiment.

DETAILED DESCRIPTION OF THE EXAMPLE EMBODIMENTS

Figure 1:
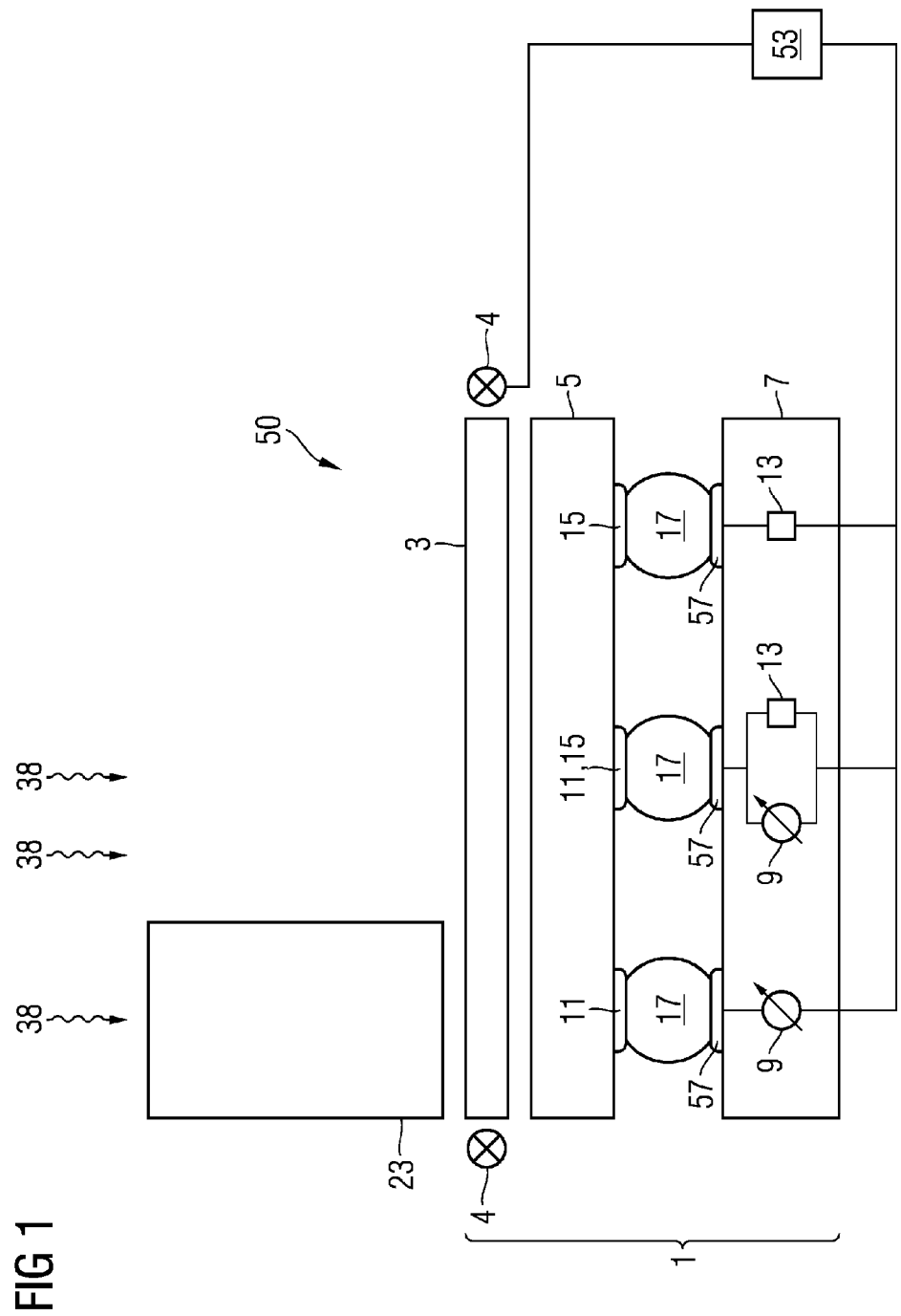
FIG. 1 shows schematically a design of a system according to the invention in a first embodiment containing an X-ray detector according to the invention in a first embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated.The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a counting X-ray detector for converting X-ray radiation into electrical signal pulses. The X-ray detector comprises in a stacked arrangement an illumination layer, a converter element and an evaluation unit. The illumination layer is designed to illuminate the converter element. The X-ray detector comprises a measuring device for ascertaining an electrical direct current component in the converter element when illumination is active. The evaluation unit comprises a counting device for ascertaining from the signal pulses a number or an energy of events.

In at least one embodiment, the illumination layer, the converter element and the evaluation unit are stacked. The illumination layer can be designed to extend parallel to the converter element such that the illumination layer spans or covers at least the converter element. The illumination layer can extend over a larger surface area than the converter element. In extent, the evaluation unit can be equal to, or smaller than, the converter element. A luminous energy emitted by light sources can be coupled into the illumination layer.

The illumination layer can comprise light sources. A luminous energy can be coupled out of the illumination layer for the additional illumination of the converter element. The light sources can emit visible or preferably infrared light. The illumination can be referred to as additional illumination. The additional illumination can take place additionally at the same time as, or at a different time from, the exposure to X-ray radiation.

The evaluation unit may be in the form of an evaluation and/or readout unit. The evaluation unit comprises a counting device. The X-ray detector comprises a measuring device. The evaluation unit or the voltage supply for applying a voltage to the converter element can comprise the measuring device.

The anode can be in the form of a pixelated electrode. The counting electrode can be assigned to a detector element, which can be designed to ascertain from the signal pulses a number and/or an energy of events. The detector element may be a sub-pixel of a macro-pixel. The measuring device is designed to ascertain an electrical direct current component in the converter element. The direct current component can take the form of a current or current flow that is approximately constant over time or has a low frequency. The direct current component can be a measure for the incident luminous energy from the additional illumination.

The direct current component can vary depending on the state of the converter element. The state may be a drift state, a temperature state or a polarization state. The dependency may be in the form of a proportionality, possibly with an offset. Unlike the electrical signal pulses, the direct current component cannot be used for counting events or for ascertaining the energy of events.

The measuring device can be used to ascertain a direct current component through the converter element. The direct current component can be a current or a current flow. A digital value can be provided as an output signal from the measuring device, from which value the current intensity or the current flow can be determined. The direct current component can be output as an absolute value or relative value. The relative value can relate the measured direct current component to another, uncalibrated value for the purpose of normalization in order to be able to give a relative increase in the current flow.

The counting device ascertains from the signal pulses a number and/or an energy of events. The events may be X-ray quanta, at least some of which are absorbed in the converter element. A number of events and/or the energy of events can be ascertained from a signal pulse. Analog and digital processing units in the evaluation unit can be used to perform the ascertainment and to provide the result of the ascertainment.

Continuous monitoring of the current flow or direct current component through small sub-units of the X-ray detector can advantageously be performed, so that an improved test and analysis facility can be provided during operation or outside of operation. The measuring device can be used to measure changes in DC conductance during the exposure to X-ray radiation. The power dissipation levels can be determined from the changes in DC conductance in the converter element and used as a process variable for temperature stabilization. The closed-loop control by way of ascertaining the direct current component can be performed in the evaluation unit instead of, or in addition to, using a temperature diode. The current for adjusting the light source can be adapted using a method according to the invention such that a comparable or equal direct current component flows through each module.

The additional illumination can advantageously be adjusted by ascertaining the direct current component. Influences from adjacent detector modules and/or adjacent illumination layers can advantageously be measured and taken into account in the adjustment. Ascertaining the direct current component can advantageously be used for analysis and monitoring purposes. The direct current component can advantageously be used as the process variable for controlling the temperature. The direct current component can advantageously be used as the starting point or parameter for correcting a count rate.

The additional illumination can be adjusted by being able to set the same current flowing through the light sources for each detector module. This has the disadvantage that the efficiency of the coupling-in of the light into the sensor can vary according to the production batch. A possible result of this is that for supposedly identical additional illumination, a different direct current component is generated, which can lead to different stability behavior of the detector modules. Setting the same current flowing through the light sources has proved very imprecise and not practicable. Advantageously, by ascertaining according to the invention the direct current component and adjusting the additional illumination on the basis thereof, it is possible to eliminate or reduce these disadvantages. The measuring device according to the invention can be used advantageously to achieve a more even or more uniform additional illumination compared with manual adjustment.

According to at least one embodiment of the invention, the evaluation unit comprises the measuring device, a measuring electrode is formed on the converter element, and an electrically conducting connection is formed between the measuring electrode and the measuring device.

The measuring device and the counting device can here be assigned to the same electrode or to a different electrode. The pixelated electrode can here comprise a measuring electrode. The pixelated electrode can comprise the measuring electrode and the counting electrode. The measuring electrode can be assigned to a detector element. The measuring electrode can be assigned to a guard ring or to a detector element designed to ascertain the direct current component, and/or the measuring electrode can form the guard ring or part of the structure of the guard ring. The guard ring or the detector element designed to ascertain the direct current component can be used solely for ascertaining the direct current component. The guard ring or the detector element designed to ascertain the direct current component can be designed not to ascertain from the signal pulses a number and/or an energy of events, and therefore the guard ring or the detector element designed to ascertain the direct current component can be unsuitable for ascertaining from the signal pulses a number and/or an energy of events, for example by not forming any electrically conducting connection to a counting electrode.

A combination of measuring electrode and counting electrode can be formed, which can be designed to ascertain the direct current component. Counting electrode and measuring electrode can be assigned to different detector elements; for example the measuring electrode can be designed as a guard ring or as an electrode of the detector element designed to ascertain the direct current component, and the counting electrode can be designed as an electrode for a detector element for ascertaining from the signal pulses a number or an energy of events. The combination of measuring electrode and counting electrode can be assigned to a detector element.

The measuring electrode can be used for ascertaining the direct current component, wherein the measuring electrode is connected to the measuring device by an electrically conducting connection. The electrically conducting connection can be in the form of a solder joint or an electrically conducting adhesive bond.

There can be a plurality of measuring devices formed in the evaluation unit. The plurality of measuring devices can be arranged in an irregular or preferably uniform distribution over the surface of the evaluation unit. A measuring device can be assigned to the macro-pixel, which may comprise a plurality of sub-pixels. A measuring device can be assigned to the sub-pixel. A measuring device can be assigned to a plurality of macro-pixels or a plurality of sub-pixels. There can be at least one measuring device formed in the evaluation unit. The measuring device can be formed as an analog measuring device in the evaluation unit. Known encoding forms can be used, for instance from known evaluation units of counting X-ray detectors or from sigma-delta converters. The output signal can be integrated in the readout data stream from the evaluation unit.

A measuring device for ascertaining a relative direct current component can be provided in the evaluation unit, which device measures the current flow through a guard ring, through at least one detector element designed to ascertain the direct current component or in at least one detector element. Owing to process variations in wafer fabrication, for instance what are known as "device-to-device" or "lot-to-lot" variations, it may be necessary to calibrate the measuring device. The calibration can be performed during the "wafer test", which is the final test after fabrication of the evaluation unit, and the calibration values can be permanently saved or hard-coded in the evaluation unit using eFuses. The invention can allow a multiplicity of measuring devices within one evaluation unit or within one detector module. The incident radiation from immediate neighbors can be taken into account in the adjustment of the illumination of the detector modules.

The sensor current induced by the additional illumination can advantageously be measured for the X-ray detector, the detector module or sub-units of the X-ray detector or of the detector module individually. The measuring device can advantageously allow the direct current component to be ascertained with a spatial resolution within a detector module.

Ascertaining the direct current component can advantageously be performed in the evaluation unit. By implementing the measuring device in the evaluation unit, the measuring device can be provided in each evaluation unit that is produced. It can advantageously be achieved that the measuring device is provided at low cost.

More than one measuring device can advantageously be provided in the evaluation unit and in a spatially distributed manner, for instance in a plurality of detector elements or in association with a plurality of detector elements or macro-pixels. A factory-calibration of the measuring device can advantageously be carried out that is intended to satisfy the requirements for adjusting the additional illumination. The direct current component can advantageously be ascertained for sub-units of the detector device, of the detector module or of the X-ray detector.

According to at least one embodiment of the invention, a direct current component induced through the converter element by the illumination can be ascertained. The additional illumination can induce a direct current component in the converter material. The direct current component can be output at the signal output of the measuring device. The effect of the additional illumination on the converter element can advantageously be ascertained.

According to at least one embodiment of the invention, a direct current component through the converter element can be ascertained while the converter element is exposed to the X-ray radiation. The direct current component can be output at the signal output. The direct current component can advantageously be measured during operation. Continuous monitoring over time of the direct current component is advantageously possible.

According to at least one embodiment of the invention, the measuring electrode is enclosed by a guard ring. In addition to its function of stabilizing the electric field, the guard ring can advantageously be used to ascertain the direct current component. Advantageously, a combination of measuring device and counting device is not needed. The guard ring can enclose at least one detector element. For example, the guard ring can enclose a macro-pixel containing 4×4 sub-pixels. The guard ring can be mounted in a region of the converter material that is screened by an anti-scatter grid.

According to at least one embodiment of the invention, the measuring electrode is an electrode of a detector element designed to ascertain the direct current component. The detector element designed to ascertain the direct current component can be a detector element without an assigned counting device. The detector element designed to ascertain the direct current component can be arranged spatially close to the guard ring or in a recess or a relief in the guard ring. The detector element designed to ascertain the direct current component can advantageously have solely the function of ascertaining a direct current component. The detector element designed to ascertain the direct current component can be screened from incident X-ray radiation via an anti-scatter grid.

According to at least one embodiment of the invention, the guard ring or the detector element designed for ascertainment is screened from directly incident X-ray radiation. The guard ring or the detector element designed for ascertainment can be screened from directly incident X-ray radiation via an anti-scatter grid. It is advantageously possible to ascertain the direct current component without any, or barely any, influence from the X-ray radiation. The direct current component can advantageously be ascertained while the X-ray radiation is incident on the X-ray detector. The guard ring or the detector element designed for ascertainment can be arranged such that the X-ray radiation is almost completely absorbed by the anti-scatter grid.

According to at least one embodiment of the invention, the measuring electrode is formed in combination with a counting electrode, with the counting electrode being connected to the counting device in an electrically conducting manner. The counting electrode and the measuring electrode are assigned to a detector element. The counting device and the measuring device are connected to the combination of counting electrode and measuring electrode in an electrically conducting manner. The counting electrode and the measuring electrode can be formed as a common electrode. A detector element can advantageously be designed to ascertain the direct current component and to ascertain from the signal pulses a number or an energy of events.

According to at least one embodiment of the invention, with regard to the combination of measuring electrode and counting electrode, the counting device and/or the measuring device can be selected. It is advantageously possible to ascertain the direct current component under the influence of X-ray radiation while ascertaining a number or energy of events. The current produced in the converter material by the X-ray radiation can be estimated and subtracted. The direct current component can advantageously be ascertained in the detector element without the influence of X-ray radiation. The direct current component can advantageously be ascertained with particularly good spatial resolution. The counting device can advantageously be operated alone under the influence of X-ray radiation. A choice between the measuring device and the counting device can advantageously be made flexibly as required.

According to at least one embodiment of the invention, the X-ray detector in the stacked arrangement also comprises a heating unit and/or a cooling unit. The heating unit and/or the cooling unit can be controlled via the ascertained direct current component. Stable operation of the X-ray detector can advantageously be achieved. In particular, the heating unit or the cooling unit can have a planar design. The heating unit or the cooling unit can be located in the stacked arrangement. The heating unit or the cooling unit can be mounted over the surface of the converter element. The heating unit or the cooling unit can be formed in the evaluation unit. The heating unit or the cooling unit can be formed on the face of the evaluation unit that faces away from the X-ray radiation, for instance on an additional substrate. The heating unit or the cooling unit can be embodied as a Peltier element. The heating unit can be embodied as an electrically conducting layer, wherein the temperature of the heating unit can be controlled using a current that can be applied.

At least one embodiment of the invention also generally relates to a detector module comprising at least one X-ray detector according to at least one embodiment of the invention. A plurality of measuring devices can advantageously be formed in the detector module in order to obtain information about the direct current component that is as spatially precise as possible.

At least one embodiment of the invention also relates to a system comprising an X-ray detector or a detector module and to a control system, wherein the direct current component is an input signal to the control system. The control system can be an open-loop control system. The control system can control the additional illumination and/or the temperature. The control can advantageously be performed in spatial proximity to the X-ray detector and without long-distance data transfer.

According to at least one embodiment of the invention, the input signal is not affected by incident X-ray radiation. The input signal to the control system can advantageously be unaffected by, or independent of, incident X-ray radiation. The ascertainment can be performed while the radiation source is not operating. The ascertainment can be performed during operation of the radiation source in a region screened from the X-ray radiation by the anti-scatter grid, for example in the guard ring or in a detector element designed to ascertain the direct current component. Simplified adjustment of the illumination is advantageously possible.

At least one embodiment of the invention also relates to a medical apparatus comprising an X-ray detector according to at least one embodiment of the invention or a detector module according to at least one embodiment of the invention or a system according to at least one embodiment of the invention. A homogeneous or uniform state of the X-ray detectors inside the detector device can advantageously be achieved. Artifacts in the imaging can advantageously be prevented or reduced.

At least one embodiment of the invention also relates to a method for stabilizing a state of a converter element, of an X-ray detector or of a detector module, comprising the steps of illumination, ascertainment and adjustment. In the illumination step, the converter element is illuminated by a first luminous energy, which is emitted by the illumination layer. In the ascertainment step, a direct current component in the converter element is ascertained when illumination is active. In the step of adjusting a second luminous energy of an illumination and/or a temperature of a heating element as a function of the ascertained direct current component, the temperature or the illumination can be adjusted.

In the illumination step, the converter element is illuminated by a luminous energy. The luminous energy can be adjusted by way of the current through the light source. In the ascertainment step, the direct current component induced in the converter element by the luminous energy is ascertained. In the adjustment step, the luminous energy and/or the temperature are adjusted. The heating element can be controlled by controlling the voltage supply to the heating element.

The method may need to be used as part of monitoring during operation of the X-ray detector. The method may be used as part of a calibration needed once or at periodic intervals. An optimum luminous energy of the additional radiation can be determined as a function of the direct current component. The aim is to achieve a direct current component that is constant over time and in space. A target range or limits can be specified to achieve this aim.

The method according to at least one embodiment of the invention can be performed by a unit, for example a computer, a microcontroller or an FPGA. The unit can be designed for data processing and for controlling or influencing the additional illumination. The unit can also provide a memory for monitoring or reusing values. The correction can be performed in real time, preferably in the evaluation unit or the FPGA, or after the data readout from the evaluation unit.

Ascertaining the direct current component can constitute an important analysis or monitoring function in the event of a fault or for testing during the manufacture of a medical apparatus. In the ascertainment step, the absolute or relative direct current component, for example through a sub-unit of the detector module, can be ascertained. The method according to the invention can advantageously be performed fully automatically; there is no need for user interactions or tedious manual fine-tuning.

According to at least one embodiment of the invention, the step of ascertaining the direct current component in the converter element is performed by a measuring electrode formed on the converter element and by a measuring device in an evaluation unit. The measuring device advantageously allows the direct current component to be ascertained continuously during operation.

According to at least one embodiment of the invention, the step of ascertaining the direct current component in the converter element is performed by a voltage supply for applying a voltage to the converter element. The method according to the invention can advantageously be implemented using the voltage supply, which is present anyway, for applying a voltage to the converter element.

According to at least one embodiment of the invention, the method is iterative.

The luminous energy incident on the detector modules can be adjusted systematically using an iterative method based on nested intervals. The aim here can be that in the absence of X-ray radiation, the same direct current component flows through all the detector modules. In this method, a starting interval, which is the same size for all the detector modules, for instance an interval of +/−100 percent of the expected luminous energy, can be set initially for the luminous energy.

The following steps can then be performed sequentially for each detector module:

Calculate the mean value of the present interval of the luminous energy;

Adjust the luminous energy to this mean value;

Stabilize the induced direct current component, wherein the time period may be several seconds, for example;

Check whether the direct current component is greater than or less than the target current; and Adjust a luminous energy on the basis of the check, wherein for too large a direct current component, the upper limit of the interval is moved to the previously calculated mean value of the previously applied interval, and for too small a direct current component, the lower limit is moved to the previously calculated mean value of the previously applied interval.

These steps can be performed for all the detector modules. Then the steps can be repeated for all the detector modules, and the method repeated until, for example, the target current is achieved within a small tolerance for all the modules, until a fixed number of iterations has been performed, or until the interval for the luminous energy cannot be reduced any further for technical reasons, in particular if the luminous energy can only be adjusted to integer values.

The method according to at least one embodiment of the invention can result in the same total current, composed of direct current component and dark current, flowing through each detector module. If the aim is for the same direct current component to flow through each module, then dark currents, which flow through the converter element even without any additional illumination, must be taken into account. Specifically this can mean that a separate target current can be specified for each module, the target current being the sum of the target current that is common to all the modules, in particular the direct current component, and the module-specific dark current.

Crosstalk effects of the additional illumination between the detector modules are reduced by the gradual restriction of the luminous energy to a narrower range and the successive, iterative procedure from detector module to detector module. Deviations from the target value of the direct current component of less than 3 percent maximum can advantageously be achieved.

According to at least one embodiment of the invention, the method additionally comprises the step of correcting a count rate of a number or an energy of events as a function of the ascertained direct current component.

The count rate can be corrected directly in the evaluation unit, in the downstream electronics, in an FPGA or in an external computer. The count rate can be determined from the signal pulses. The count rate can be a count rate of all the events above an energy threshold. The count rate can be a count rate of all the events within an energy window. The correction can be performed on the basis of a correction table or a predetermined correction polynomial. The correction polynomial can contain information about the change in count rates as a function of the temperature or the illumination.

The total current through the converter element is proportional to the heat produced in the converter element. Since the measured count rate of the converter element depends on the temperature, ascertaining the direct current component can also be used to correct this temperature effect. The power dissipation in the converter element and consequently the temperature change can be determined from the current measurement. This can be used advantageously to correct the count rate.

FIG. 1 shows an example implementation of the system 50 according to the invention in a first embodiment containing the X-ray detector 1 according to the invention in a first embodiment. The X-ray detector 1 comprises in a stacked arrangement an illumination layer 3, a converter element 5 and an evaluation unit 7. The illumination layer 3 is an illumination element bounded in three dimensions. A luminous energy emitted by the light sources 4 is coupled into the illumination layer 3. The light sources 4 may be located at the sides of the illumination layer 3. The illumination layer 3 can extend over a larger surface area than the converter element 5. Light can be coupled out of the illumination layer 3 (e.g. via suitable structures in the illumination layer 3), and used for illuminating the converter element 5.

On the face that faces away from the direction of incidence of the X-ray radiation 38, the converter element 5 comprises an electrode, which comprises the measuring electrodes 11 and the counting electrodes 15. The central measuring electrode 11 is combined with a counting electrode. The measuring electrodes 11 and the counting electrodes 15 are connected to the evaluation unit 7 by an electrically conducting connection 17. The electrically conducting connections 17 are in the form of solder joints.

A readout contact 57 is provided between the electrically conducting connection 17 for making electrically conducting contact with the evaluation unit 7. The measuring electrode 11 located on the left is assigned to a measuring device 9 in the evaluation unit 7. The counting electrode 15 located on the right is assigned to a counting device 13 in the evaluation unit 7. The combination of counting electrode 15 and measuring electrode 11 is assigned to a counting device 13 and to a measuring device 9, with it being possible to select the counting device 13 and/or the measuring device 9. The output signal from the measuring devices 9 and possibly from the counting devices 13 is fed to a control system 53, which adjusts or controls the luminous energy as a function of the ascertained direct current component.

Above the face of the illumination layer 3 that faces the X-ray radiation 38 is arranged an anti-scatter grid 23, which screens the region of the converter element 5 lying thereunder from incident X-ray radiation 38. The measuring electrode 11 can be embodied as a guard ring or as a detector element designed to ascertain the direct current component. The combination of counting electrode 11 and measuring electrode 15 is embodied as an electrode of a detector element. The counting electrode 15 is embodied as an electrode of a detector element.

Figure 2:
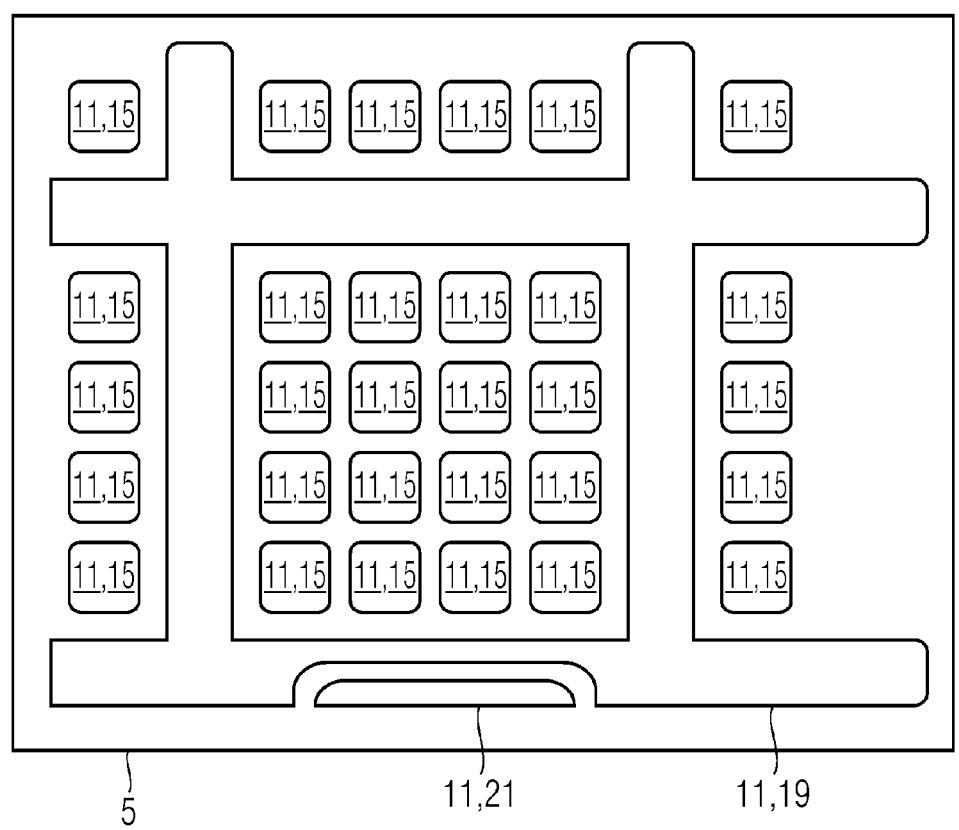
FIG. 2 shows schematically a design of an electrode according to an embodiment of the invention.

FIG. 2 shows an example embodiment of the electrode according to the invention. The electrode is embodied as an anode on the face of the converter element 5 that faces away from the X-ray radiation. The counting electrodes 15 and measuring electrodes 11 in a 4×4 combination are embodied as 4×4 detector elements enclosed by a guard ring 19. The guard ring 19 can be formed in the region that is in the shadow of the anti-scatter grid. The guard ring 19 is a measuring electrode 11. The electrode 21 designed to ascertain the direct current component is assigned to a detector element designed to ascertain the direct current component. The electrode 21 designed to ascertain the direct current component is a measuring electrode 11.

Figure 3:
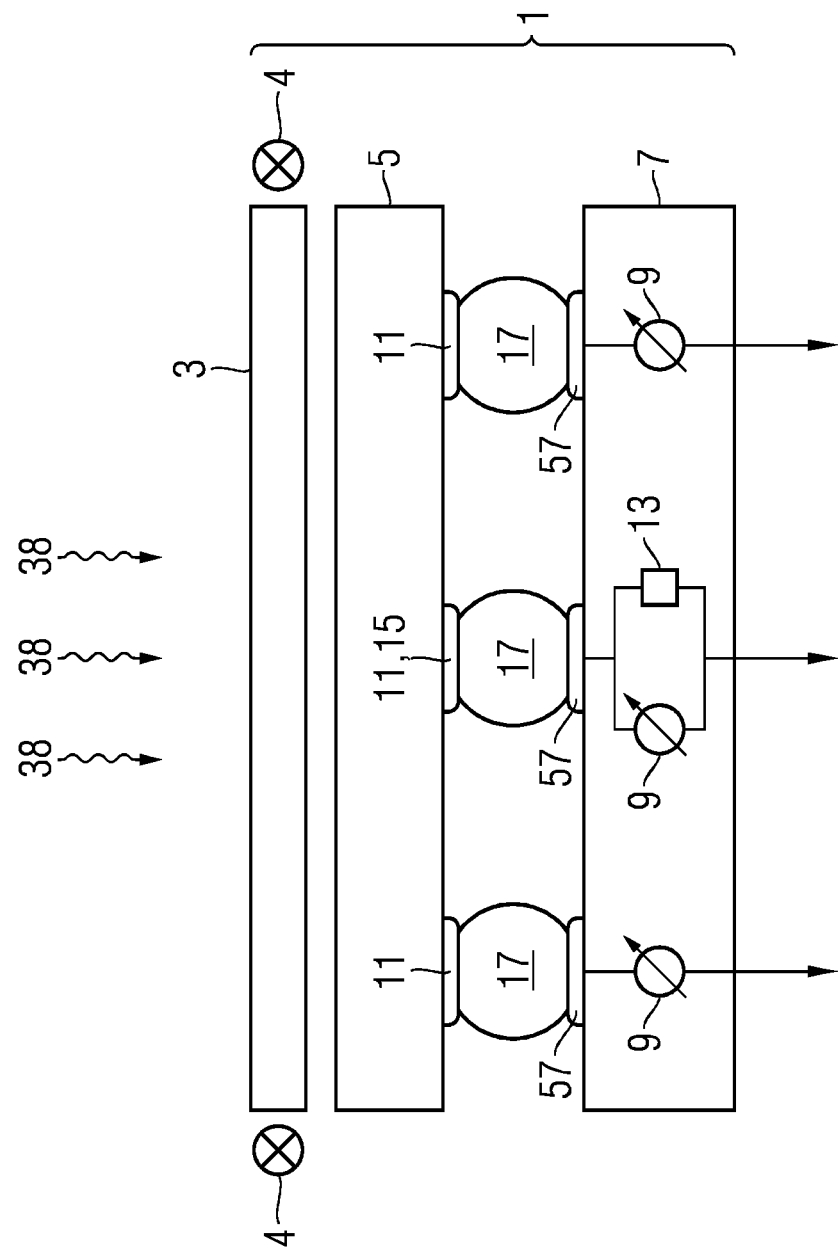
FIG. 3 shows schematically a design of an X-ray detector according to the invention in a second embodiment.

FIG. 3 shows an example implementation of the X-ray detector 1 according to the invention in a second embodiment. Unlike FIG. 1, the X-ray detector 1 does not comprise an anti-scatter grid, at least not in the region shown. A combined counting electrode 15 and measuring electrode 11 is shown in the center. Measuring electrodes 11 are shown on the right and left sides. Counting electrodes 15 and measuring electrodes 11 can be arranged alternately or in groups. The detector elements assigned to the measuring electrodes 11 and/or counting electrodes 15 are not screened from X-ray radiation 38.

Figure 4:
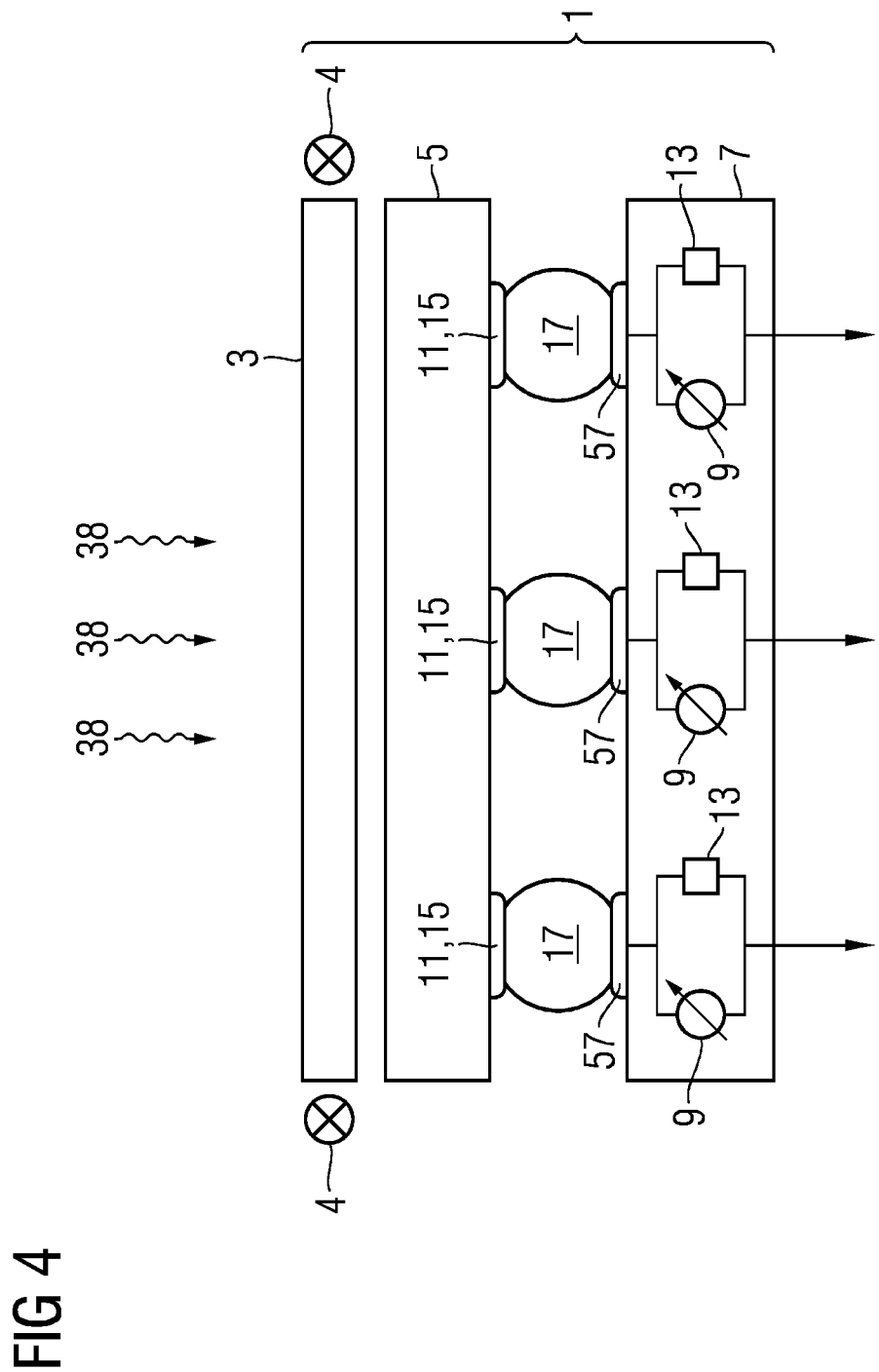
FIG. 4 shows schematically a design of an X-ray detector according to the invention in a third embodiment.

FIG. 4 shows an example implementation of the X-ray detector 1 according to the invention in a third embodiment. Unlike FIG. 3, the X-ray detector 1 comprises solely the combination of counting electrodes 15 and measuring electrodes 11. All the detector elements are designed to ascertain the direct current component and to ascertain a number and/or energy of events.

Figure 5:
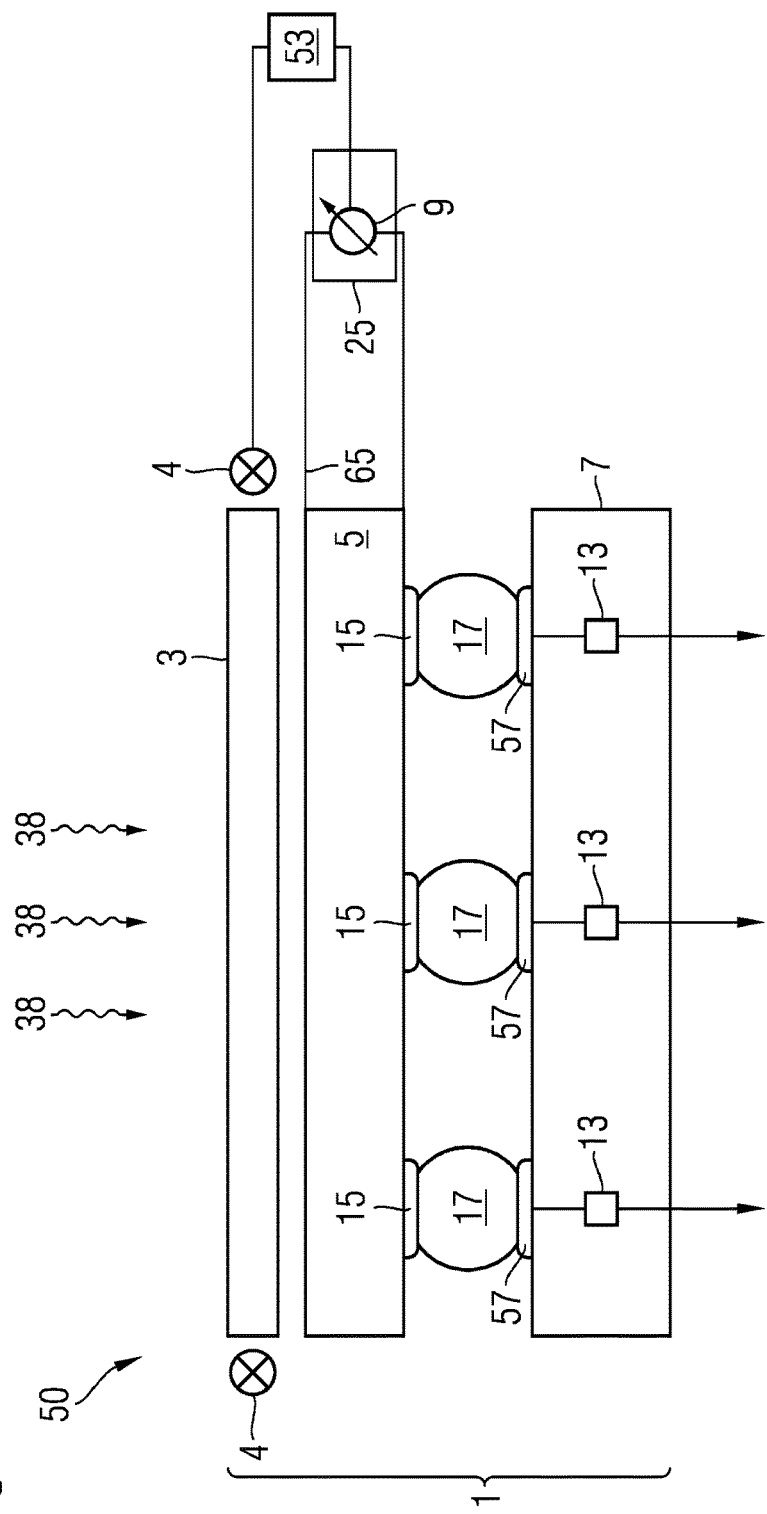
FIG. 5 shows schematically a design of a system according to the invention in a second embodiment containing an X-ray detector according to the invention in a fourth embodiment.

FIG. 5 shows an example implementation of the system 50 according to the invention in a second embodiment containing the X-ray detector 1 according to the invention in a fourth embodiment. The measuring device 9 is formed in a voltage supply 25 for applying a voltage or a high voltage to the converter element 5. The voltage supply 25 comprises a sensor voltage supply line 65 to the face of the converter element 5 that faces the X-ray radiation 38. The output signal from the measuring device 9 is fed to a control system 53, which adjusts or controls the luminous energy as a function of the ascertained direct current component.

Figure 6:
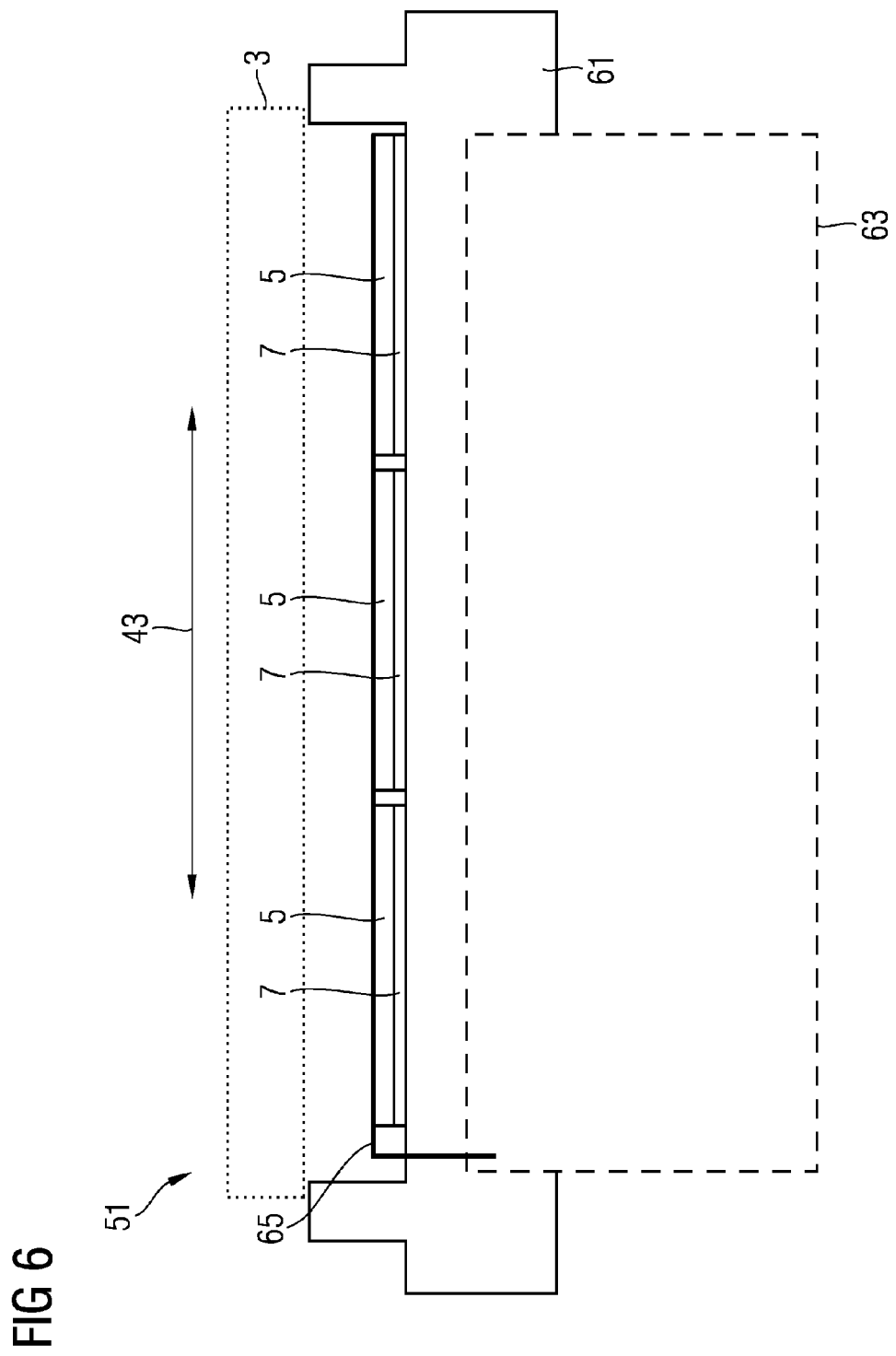
FIG. 6 shows schematically a design of a detector module according to an embodiment of the invention.

FIG. 6 shows an example implementation of the detector module 51 according to an embodiment of the invention in a side view parallel to the direction of rotation 43. The X-ray detectors 1 are mounted together with the module electronics 63 and the illumination layer 3 on a module mechanical structure 61. The illumination layer 3 can alternatively be formed in direct contact with the converter element. In this design, the illumination layer 3 covers the entire depth along the direction of rotation 43 of the detector module 51.

Figure 7:
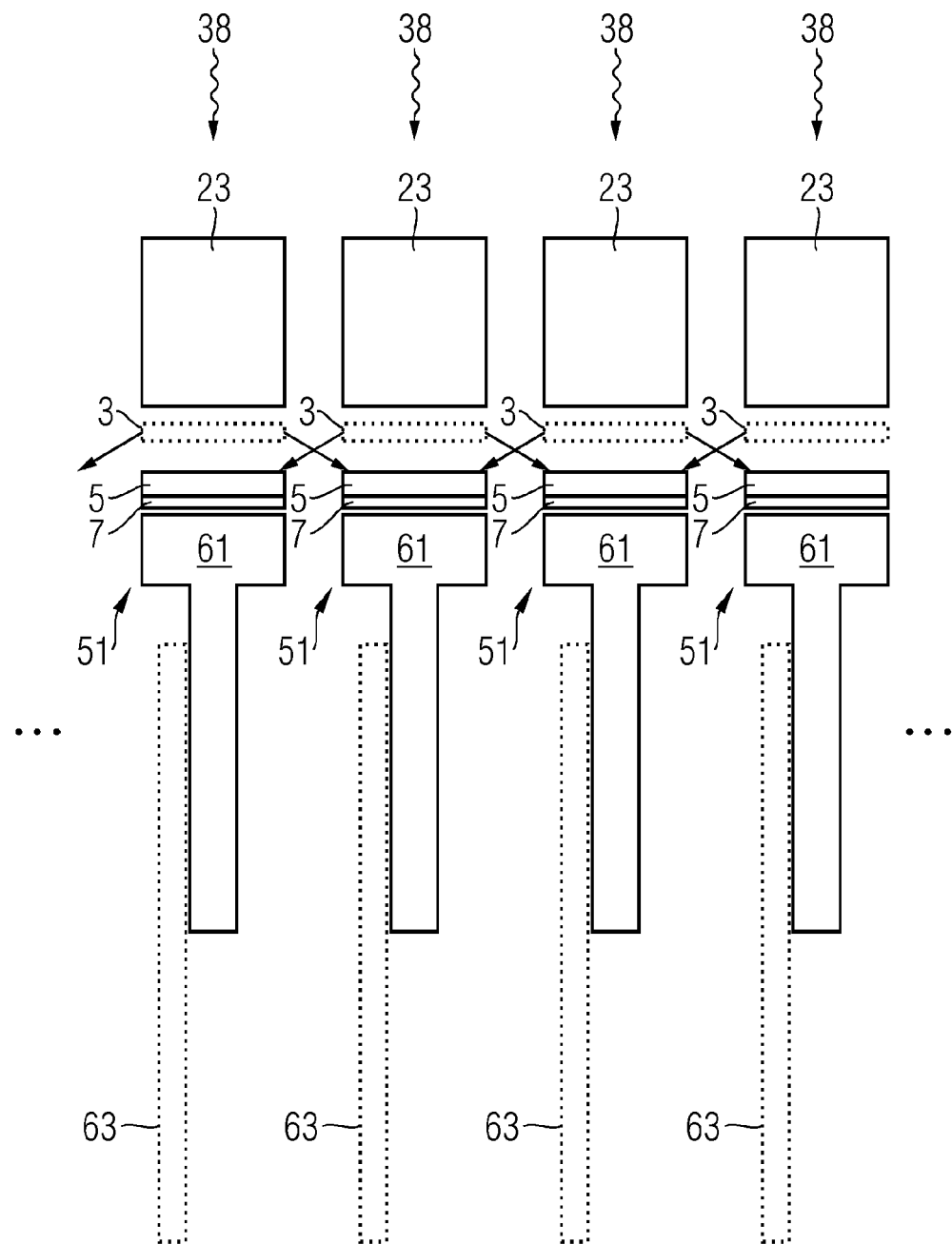
FIG. 7 shows schematically a design of a plurality of adjacent detector modules according to an embodiment of the invention.

FIG. 7 shows an example implementation of a plurality of adjacent detector modules 51 according to an embodiment of the invention. Four adjacent detector modules are shown by way of example. The view is shown perpendicular to the axis of rotation. The anti-scatter grid 23 is designed such that the detector elements are shielded from incident radiation scattered from the X-ray radiation while at the same time are able to register X-ray radiation 38 that is directly incident. The arrows between the detector modules 51 indicate that not only light from the illumination layer 3 belonging to the module itself is incident on the converter element 5 but also the light from adjacent detector modules 51. The detector modules 51 can be arranged in a radial direction at an angle not equal to 0 degrees so that a curved detector device can be achieved.

Figure 8:
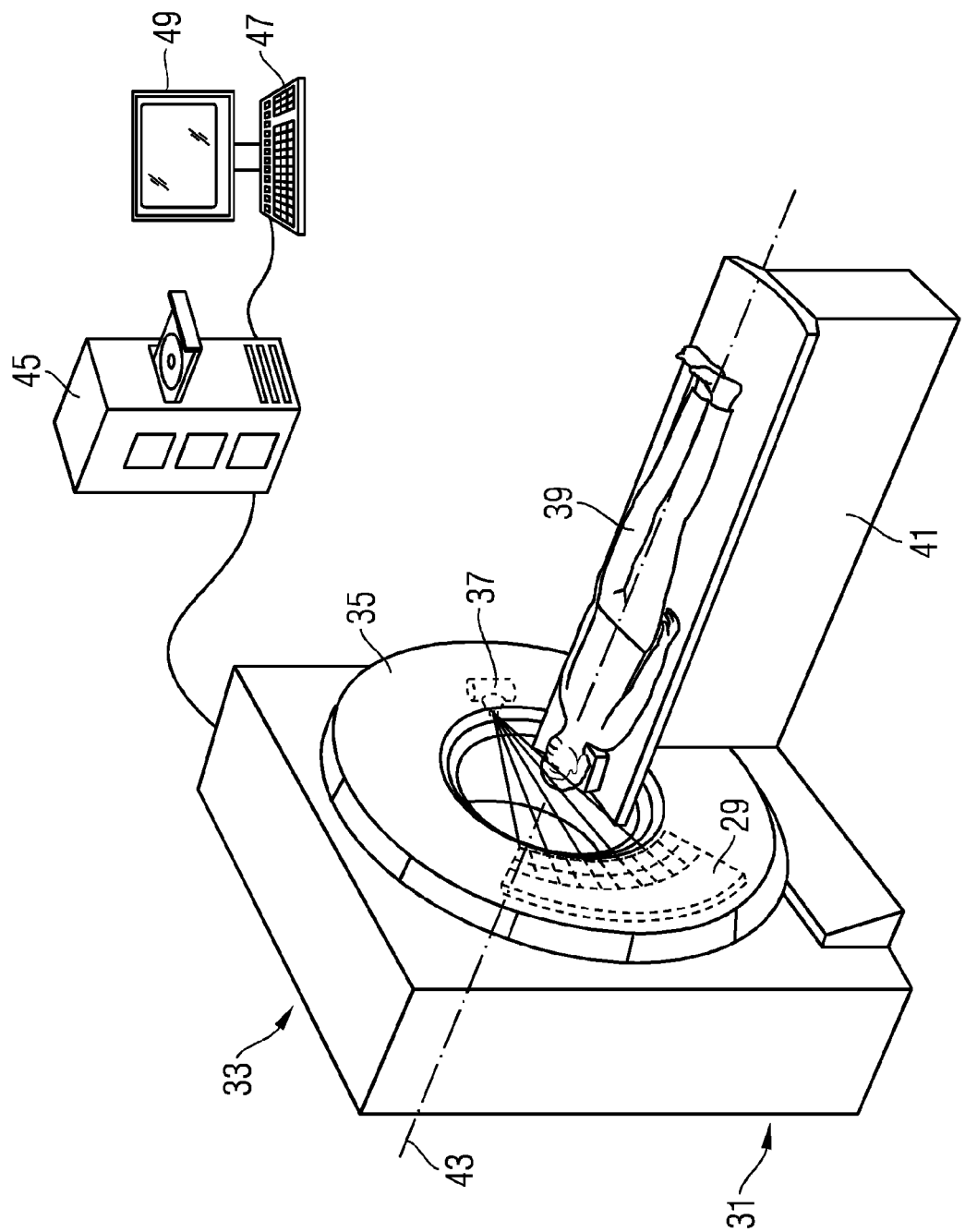
FIG. 8 is a schematic diagram of a computed tomography machine according to an embodiment of the invention.

FIG. 8 shows an example implementation of the computed tomography machine 31 according to an embodiment of the invention comprising a detector device 29. The detector device 29 comprises the X-ray detector according to an embodiment of the invention. The detector device 29 can comprise a plurality of detector modules comprising at least one X-ray detector. The detector modules 51 preferably comprise a plurality of X-ray detectors in a two-dimensional matrix or array. The computed tomography machine 31 contains a gantry 33 having a rotor 35. The rotor 35 comprises an X-ray source 37 and the detector device 29 according to an embodiment of the invention. The patient 39 is supported on the patient couch 41 and can be moved along the axis of rotation z 43 by the gantry 33. A processing unit 45 is used to control and compute the sectional images. An input device 47 and an output device 49 are connected to the processing unit 45.

FIG. 9 shows an example implementation of the method 70 according to the invention in a first embodiment. In the illumination step 71, the converter element is illuminated by a first luminous energy, which is emitted by the illumination layer. In the ascertainment step 73, a direct current component in the converter element is ascertained using a measuring electrode formed on the converter element and using a measuring device in an evaluation unit, or using a voltage supply 25 for applying a voltage to the converter element 5. In the step of adjusting 75 a second luminous energy of an illumination and/or a temperature of a heating element as a function of the ascertained direct current component, the temperature or the illumination can be adjusted. The luminous energy can be adjusted via a current through the light source, for instance a current through a light emitting diode, or at the light source. In the ascertainment step 73, the direct current component induced in the converter element by the luminous energy is ascertained. The heating element can be controlled by controlling the voltage supply to the heating element.

FIG. 10 shows an example implementation of the method 70 according to the invention in a second embodiment. The method 70 according to the invention in the second embodiment is an iterative method. The luminous energy incident on the detector modules is adjusted systematically using an iterative method based on nested intervals. The aim here is that the same direct current component flows through all the detector modules in the absence of X-ray radiation. In this method, a starting interval, which is the same size for all the detector modules, for instance an interval of +/−100 percent of the expected luminous energy, is set initially for the luminous energy.

The illumination step 71 comprises the following steps:
Calculate the mean value of the present interval of the luminous energy;
Adjust the luminous energy to this mean value, and illuminate; and
Stabilize the induced direct current component, where the time period may be several seconds, for example.

The ascertainment step 73 comprises a step of checking whether the direct current component is greater than or less than the target current. The adjustment step 75 comprises adjusting a luminous energy on the basis of the check, where for too large a direct current component, the upper limit of the interval is moved to the previously calculated mean value of the previously applied interval, and for too small a direct current component, the lower limit is moved to the previously calculated mean value of the previously applied interval. The adjusted luminous energy may be a second luminous energy or luminous energy that is different from the previously set luminous energy in the illumination step.

These steps are performed for all the detector modules. Then the steps are repeated in the same order for all the detector modules, indicated by the arrow in the figure, and the method repeated until, for example, the target current is reached within a small tolerance for all the modules, until a fixed number of iterations have been performed, or until the interval for the luminous energy cannot be reduced any further for technical reasons, in particular if the luminous energy can only be adjusted to integer values. The ascertainment step 73 may be the last step, for instance when the target current is achieved within a small tolerance for all the modules.

FIG. 11 shows an example implementation of the method 70 according to the invention in a third embodiment. The method 70 additionally comprises the step of correcting a count rate of a number or an energy of events as a function of the ascertained direct current component. The count rate can be corrected directly in the evaluation unit, in the downstream electronics, in an FPGA or in an external computer. The correction in the correction step can be performed on the basis of a correction table or a predetermined correction polynomial. The correction polynomial can contain information about the change in count rates as a function of the temperature or the illumination. The total current through the converter element is proportional to the heat produced in the converter element. Since the measured count rate of the converter element depends on the temperature, the ascertained direct current component is used to correct this temperature effect. The power dissipation in the converter element and consequently the temperature change can be determined from the current measurement. The count rate is corrected by determining the temperature change.

Although the invention has been illustrated in greater detail using the preferred example embodiment, the invention is not limited by the disclosed examples, and a person skilled in the art can derive other variations therefrom without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector module having a plurality of counting X-ray detectors arranged in a stacked arrangement, for converting X-ray radiation into signal pulses, the detector module comprising:
   a controller; and each of the plurality of counting x-ray detectors having an illumination layer;
      a converter element, the illumination layer being designed to illuminate the converter element;
      an evaluation unit;
      a measuring device to ascertain electrical direct current components as signal pulses in the converter element when illuminated, the evaluation unit including a counting device to ascertain from the signal pulses, a number or an energy of events, wherein
   the controller receives the signal pulses from the measuring device and is configured to control illumination emitted from the illumination layer such that a direct current component induced in the plurality of converter elements is the same.

2. The X-ray detector of claim 1, wherein the evaluation unit includes the measuring device, a measuring electrode formed on the converter element, and an electrically conducting connection formed between the measuring electrode and the measuring device.

3. The X-ray detector of claim 2, wherein the measuring electrode is enclosed by a guard ring.

4. The X-ray detector of claim 3, wherein the guard ring or the detector element designed for ascertainment is screened from directly incident X-ray radiation.

5. The X-ray detector of claim 2, wherein the measuring electrode is an electrode of a detector element designed to ascertain the direct current component.

6. The X-ray detector of claim 5, wherein the guard ring or the detector element designed for ascertainment is screened from directly incident X-ray radiation.

7. The X-ray detector of claim 2, wherein the measuring electrode is formed in combination with a counting electrode, and wherein the counting electrode is connected to the counting device in an electrically conducting manner.

8. The X-ray detector of claim 7, wherein with regard to the combination of measuring electrode and counting electrode, at least one of the counting device and the measuring device is selectable.

9. The X-ray detector of claim 2, wherein a direct current component, induced through the converter element by the illumination, is ascertainable.

10. The X-ray detector of claim 9, wherein the measuring electrode is enclosed by a guard ring.

11. The X-ray of claim 2, wherein a direct current component through the converter element is ascertainable while the converter element is exposed to the X-ray radiation.

12. The X-ray detector of claim 11, wherein the measuring electrode is an electrode of a detector element designed to ascertain the direct current component.

13. The X-ray detector of claim 2, further comprising, in the stacked arrangement, at least one of a heating unit and a cooling unit.

14. A detector module comprising the X-ray detector of claim 2.

15. The X-ray detector of claim 1, wherein a direct current component, induced through the converter element by the illumination, is ascertainable.

16. The X-ray of claim 1, wherein a direct current component through the converter element is ascertainable while the converter element is exposed to the X-ray radiation.

17. The X-ray detector of claim 1, further comprising, in the stacked arrangement, at least one of a heating unit and a cooling unit.

18. A detector module comprising the X-ray detector of claim 1.

19. A system, comprising:
the detector module of claim 18; and
a control system, wherein the direct current component is an input signal to the control system.

20. A medical apparatus, comprising:
the detector module of claim 18.

21. A system, comprising:
the X-ray detector of claim 1; and
a control system, wherein the direct current component is an input signal to the control system.

22. The system of claim 21, wherein the input signal is not affected by incident X-ray radiation.

23. A medical apparatus, comprising:
the system of claim 21.

24. A medical apparatus, comprising:
the X-ray detector of claim 1.

25. A method for stabilizing a state of a plurality of converter elements of an X-ray detector or of a detector module, comprising:
illuminating the plurality of converter elements by a first luminous energy, emitted by an illumination layer of the X-ray detector or detector module;
ascertaining a direct current component in the plurality of converter elements when illuminated; and
adjusting at least one of a second luminous energy of an illumination and a temperature of a heating element as a function of the ascertained direct current component such that the direct current component is the same in the plurality of converter elements based on the direct current component.

26. The method of claim 25, wherein the ascertaining of the direct current component in the converter element is performed by a measuring electrode formed on the converter element and by a measuring device in an evaluation unit.

27. The method of claim 26, wherein the method is iterative.

28. The method of claim 25, wherein the ascertaining of the direct current component in the converter element is performed by a voltage supply for applying a voltage to the converter element.

29. The method of claim 28, wherein the method is iterative.

30. The method of claim 25, wherein the method is iterative.

31. The method of claim 25, further comprising:
correcting a count rate of a number or an energy of events as a function of the ascertained direct current component.

* * * * *